United States Patent
Kyriatsoulis et al.

(10) Patent No.: US 9,341,552 B2
(45) Date of Patent: May 17, 2016

(54) RELEASE REAGENT FOR VITAMIN D COMPOUNDS

(71) Applicant: Roche Diagnostics Operations, Inc., Indianapolis, IN (US)

(72) Inventors: Apostolos Kyriatsoulis, Weilheim i. (DE); Susanne Feldmann, Penzberg (DE); Eramus Huber, Finning (DE); Nicole Horn, Poecking (DE); Leopold von Proff, Hohenpeissenberg (DE); Uwe Kobold, Weilhelm (DE); Angela Puhlmann, Neuried (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/575,423

(22) Filed: Dec. 18, 2014

(65) Prior Publication Data

US 2015/0104876 A1   Apr. 16, 2015

Related U.S. Application Data

(60) Division of application No. 12/053,655, filed on Mar. 24, 2008, now abandoned, which is a continuation of application No. PCT/EP2006/009361, filed on Sep. 27, 2006.

(30) Foreign Application Priority Data

Sep. 29, 2005   (EP) ..................................... 05021246

(51) Int. Cl.
*G01N 33/82* (2006.01)
*G01N 1/34* (2006.01)
(Continued)

(52) U.S. Cl.
CPC ........... *G01N 1/34* (2013.01); *C07K 16/44* (2013.01); *G01N 33/52* (2013.01); *G01N 33/82* (2013.01); *Y10T 436/10* (2015.01)

(58) Field of Classification Search
CPC ...................................................... G01N 33/82
See application file for complete search history.

(56) References Cited

U.S. PATENT DOCUMENTS

| 4,816,567 A | 3/1989 | Cabilly et al. |
| 5,594,102 A | 1/1997 | Panzone et al. |

(Continued)

FOREIGN PATENT DOCUMENTS

| DE | 10144905 A1 | 10/2003 |
| EP | 0583945 A2 | 2/1994 |

(Continued)

OTHER PUBLICATIONS

Braun, A. et al., "Interaction of the vitamin D-binding protein (group-specific component) and its ligand 25-hydroxyvitamin D3: Binding differences of the various genetic types disclosed by isoelectric focusing," Electrophoresis 11, 478-483 (1990).

(Continued)

*Primary Examiner* — Benjamin Packard
(74) *Attorney, Agent, or Firm* — Roche Diagnostics Operations, Inc.

(57) ABSTRACT

The present invention concerns a reagent composition for releasing vitamin D compounds bound to vitamin D-binding protein, a method for the detection of a 25-hydroxyvitamin D compound in which the 25-hydroxyvitamin D compound is released from vitamin D-binding protein using this reagent and the mixture obtained in this manner is analyzed, the use of the reagent to release vitamin D compounds as well as a kit for detecting 25-hydroxyvitamin D which contains the reagent for releasing vitamin D compounds in addition to the usual immunological reagents.

2 Claims, 7 Drawing Sheets

(51) Int. Cl.
*C07K 16/44* (2006.01)
*G01N 33/52* (2006.01)

(56) References Cited

U.S. PATENT DOCUMENTS

| | | | |
|---|---|---|---|
| 5,714,586 A | | 2/1998 | Kunstmann et al. |
| 5,968,981 A | * | 10/1999 | Chien et al. ............. 514/557 |
| 5,981,779 A | | 11/1999 | Holick et al. |
| 2004/0054160 A1 | | 3/2004 | Pal |
| 2004/0096900 A1 | | 5/2004 | Laurie et al. |
| 2004/0132104 A1 | * | 7/2004 | Sackrison et al. ......... 435/7.1 |
| 2005/0079563 A1 | | 4/2005 | Gupta |

FOREIGN PATENT DOCUMENTS

| | | |
|---|---|---|
| EP | 0753743 B1 | 1/1997 |
| EP | 1195373 B1 | 3/2005 |
| WO | 99/67211 A1 | 12/1999 |
| WO | 02/46746 A3 | 6/2002 |
| WO | 02/057797 A2 | 7/2002 |
| WO | 03/023391 A3 | 3/2003 |
| WO | 2004/063704 A2 | 7/2004 |

OTHER PUBLICATIONS

Eisman, J. et al., "Determination of 25-Hydroxyvitamin D2 and 25-Hydroxyvitamin D3 in Human Plasma Using High-Pressure Liquid Chromatography," Analytical Biochemistry 80, 298-305 (1977).

Haddad, J. et al., "Competitive Protein-Binding Radioassay for 25-Hydroxycholecalcifrol," J. Clin Endocr 33: 992-995 (1971).

Kawakami, M. et al., "Quantitative Studies of the Interaction of Cholecalciferol (Vitamin D3) and it Metabolites with Different Genetic Variants of the Serum Binding Protein for these Sterols," Biochem. J. 179, 413-423 (1979).

Larrick, J. et al., "Recombinant Antibodies," Hum. Antibod. Hybridomas, 2, 172-189 (Oct. 1991).

McCafferty, J. et al. "Phage Antibodies: Filamentous Phage Displaying Antibody Variable Domains,"Nature, 348, 552-554 (Dec. 1990).

Opposition Proceedings document in German language dated 25 Jul. 2012 for corresponding EP Patent No. 1931999.

Roempp Chemielexikon, 9th Edition, pp. 26, 27, 983, 987 (1995).

Schmidt-Gayk, H. et al., Calcium Regulating Hormones, Vitamin D Metabolites, and Cyclic AMP, Springer-Verlag (1990), pp. 24-47.

Takagai, Y. et al., "Determination of ppb Levels of Tryptophan Derivatives by Capillary Electrophoresis with Homogeneous Liquid—Liquid Extraction and Sweeping Method," Chem. Pharm. Bulletin 51 (2003) 373-377.

Vogeser, M. et al., "Candidate Reference Method for the Quantification of Circulating 25-Hydroxyvitamin D3 by Liquid Chromatography-Tandem Mass Spectrometry," Clinical Chemistry 50:8, 1415-1417 (2004).

Zerwekh, J., "The Measurement of Vitamin D: Analytical Aspects," Ann Clin Biochem 41, 272-281 (2004).

* cited by examiner

RELEASE REAGENT FOR VITAMIN D COMPOUNDS

RELATED APPLICATIONS

This application is a divisional of U.S. application Ser. No. 12/053,655 filed Mar. 24, 2008, which is a continuation of PCT/EP2006/009361 filed Sep. 27, 2006 and claims priority to EP 05021246.3 filed Sep. 29, 2005, the disclosures of which are hereby incorporated by reference in their entirety.

FIELD OF THE INVENTION

The present invention concerns a reagent composition for releasing vitamin D compounds bound to vitamin D-binding protein and a method for detecting a 25-hydroxyvitamin D compound in which the 25-hydroxyvitamin D compound is released from the vitamin D-binding protein by the use of this reagent and the mixture obtained in this manner is analyzed. It also concerns the use of the reagent to release vitamin D compounds as well as a kit for detecting 25-hydroxyvitamin D which contains the reagent for releasing vitamin D compounds in addition to common immunological reagents.

BACKGROUND

An adequate supply of vitamin D is vital as the term "vitamin" already suggests. A deficiency of vitamin D leads to severe diseases such as rickets or osteoporosis. While vitamin D was still regarded as a single substance at the beginning of the last century, the vitamin D system has changed in the course of the last three decades into a complex and manifold network of vitamin D metabolites. Nowadays more than 40 different vitamin D metabolic products are known (Zerwekh, J. E., Ann. Clin. Biochem. 41 (2004) 272-281).

Humans can only produce $D_3$ vitamins or calciferols by the action of ultraviolet rays from sunlight on the skin. Vitamin $D_3$ that is produced in the skin binds to the so-called vitamin D-binding protein which transports it into the liver where it is converted into 25-hydroxyvitamin $D_3$ by 25-hydroxylation. A multitude of other tissues are nowadays known to be involved in vitamin D metabolism in addition to the skin and liver, the two organs that have already been mentioned (refer to Schmidt-Gayk, H. et al. (eds.), "Calcium regulating hormones, vitamin D metabolites and cyclic AMP", Springer Verlag, Heidelberg (1990) pp. 24-47). 25-Hydroxyvitamin D and more specifically 25-hydroxyvitamin $D_2$ and 25-hydroxyvitamin $D_3$ are the central storage form of vitamin D in the human organism with regard to their amounts. When needed these precursors can be converted in the kidneys to form the biologically active 1α,25-dihydroxyvitamin D, the so-called D hormone. The biologically active vitamin D regulates among others calcium uptake from the intestine, bone mineralization, and it influences a large number of other metabolic pathways such as, e.g., the insulin system.

Measuring the vitamin D level itself is of little benefit when determining the vitamin D status of a patient because concentrations of vitamin D (vitamin $D_2$ and vitamin $D_3$) fluctuate greatly depending on food uptake. In addition, vitamin D has a relatively short biological half-life in the circulation (24 hours), and it is therefore also for this reason not a suitable parameter for determining the vitamin D status of a patient. The same also applies to physiologically active forms of vitamin D (1,25-dihydroxyvitamin D). These biologically active forms also occur in relatively small and highly fluctuating concentrations compared to 25-hydroxyvitamin D. For all these reasons, the quantification of 25-hydroxyvitamin D in particular is a suitable means to globally analyze the total vitamin D status of a patient.

The binding of 25-hydroxyvitamin D or other vitamin D compounds to the vitamin D-binding protein enormously complicates the determination of vitamin D compounds. All known methods require that the vitamin D compound to be analyzed is released or detached from the complex that it forms with the binding protein. In the following this is referred to as the release of a vitamin D compound from vitamin D-binding protein for the sake of simplification, although of course it can only be released from a complex of vitamin D compound and vitamin D-binding protein and not from the vitamin D-binding protein alone.

Since the vitamin D-binding protein has a high tendency to correctly refold, it is often necessary to firstly release vitamin D compounds and then to separate the vitamin D-binding protein from the vitamin D compounds to be analyzed.

Due to the high clinical importance of 25-hydroxyvitamin D, a large number of methods are known from the literature which allow 25-hydroxyvitamin D to be more or less reliably determined.

Haddad, J. G. et al., J. Clin. Endocrinol. Metab. 33 (1971) 992-995, and Eisman, J. A. et al., Anal. Biochem. 80 (1977) 298-305, for example, describe the determination of 25-hydroxyvitamin D concentrations in blood samples using high performance liquid chromatography (HPLC).

Other approaches for the determination of 25-hydroxyvitamin D are based, among others, on the use of vitamin D-binding proteins like those that are present in milk. Thus Holick, M. F. and Ray, R. (U.S. Pat. No. 5,981,779) and DeLuca et al. (EP 0 583 945) describe vitamin D assays for hydroxyvitamin D and dihydroxyvitamin D which are based on the binding of these substances to vitamin D-binding protein where the concentrations of these substances are determined by means of a competitive test procedure. However, a prerequisite of this method is that vitamin D metabolites to be determined firstly have to be isolated from the original blood or serum samples and have to be purified by, for example, chromatography.

Armbruster, F. P. et al. (WO 99/67211) teach that a serum or plasma sample should be prepared for vitamin D determination by ethanol precipitation. In this method the protein precipitate is removed by centrifugation, and the ethanolic supernatant contains soluble vitamin D metabolites. These can be measured in a competitive binding assay.

Alternatively, EP 753,743 teaches that the proteins can be separated from blood or serum samples using a periodate salt. In this case, vitamin D compounds are determined in the protein-free supernatant from the samples treated with periodate. In some commercial tests, acetonitrile is recommended for the extraction of serum or plasma sample (e.g., in the radioimmunoassay from DiaSorin or in the vitamin D test from the Immundiagnostik company).

In recent years a number of different release reagents were proposed which should in principle be suitable for releasing vitamin D compounds from binding protein present in the sample. However, this release or detachment should be carried out under relatively mild conditions, thus enabling a direct use of the sample treated with the release reagent in a binding test (see, for example, WO 02/57797 and US 2004/0132104). Despite immense efforts in recent years, all available methods for determining vitamin D have disadvantages such as laborious sample preparation, poor standardization, poor agreement between test procedures, or bad recovery of spiked vitamin D (see for this in particular Zerwekh, J. E., supra).

It is particularly difficult to automate a test for a vitamin D compound. The automation requires solving a very difficult problem, i.e., surviving a tightrope walk. On the one hand it is necessary to release the vitamin D compounds from vitamin D-binding protein with the aid of a suitable release reagent; on the other hand, the conditions have to be selected such that the sample can be directly analyzed further. A prerequisite of this direct further analysis is that, on the one hand, the vitamin D-binding protein does not bind or no longer to a significant extent binds to the vitamin D compounds during this analysis and thus does not interfere with this analysis and, on the other hand, that the release reagent used does not interfere with the binding of detection reagents such as antibodies to the vitamin D-binding protein to be examined. In addition, it is known that different alleles of the vitamin D-binding protein are present in the human population which behave biochemically differently. The release and measurement of vitamin D compounds should be comparable for various alleles/phenotypes.

Thus the object of the present invention was to develop a release reagent for vitamin D compounds and in particular for hydroxyvitamin D compounds which can at least partially overcome the problems of the prior art. A suitable reagent composition for releasing vitamin D compounds, a method for determining 25-hydroxyvitamin D compounds, the use of the reagent composition, and kits for the determination of 25-hydroxyvitamin D compounds using this reagent composition are described in the following and are encompassed by the attached claims.

SUMMARY OF THE INVENTION

The present invention concerns a reagent composition for releasing vitamin D compounds from vitamin D-binding protein which has a pH value of 3.8 to 4.8 and contains 5 to 30 volume percent of one or more amphiphilic reagents selected from the group comprising dimethyl sulfoxide (DMSO) and a liquid organic amide as well as optionally 0.7 to 8 volume percent of a short-chain (C1 to C3) alcohol.

Furthermore the invention concerns a method for the immunological detection of a 25-hydroxyvitamin D compound comprising the steps: a) mixing the sample to be examined with a reagent for releasing vitamin D compounds from vitamin D-binding protein which results in a mixture that has a pH value of 3.8 to 4.8 and contains 5 to 20 volume percent of one or more amphiphilic reagents selected from the group comprising dimethyl sulfoxide (DMSO) and a liquid organic amide as well as optionally 0.5 to 5 volume percent of a short-chain (C1-C3) alcohol, and b) immunological analysis of the mixture from a).

In addition it is described how the reagent composition of the present invention can be used to release vitamin D compounds from vitamin D-binding protein.

In addition a kit for detecting 25-hydroxyvitamin D is disclosed which contains the reagents necessary for the test procedure and the reagent composition according to the invention to release vitamin D compounds from vitamin D-binding protein.

DETAILED DESCRIPTION OF THE INVENTION

In a first preferred embodiment, the present invention concerns a reagent composition for releasing vitamin D compounds from vitamin D-binding protein which has a pH value of 3.8 to 4.8 and contains 5 to 30 volume percent of one or more reagents selected from the group comprising dimethyl sulfoxide (DMSO) and a liquid organic amide as well as optionally 0.7 to 8 volume percent of a short-chain (C1 to C3) alcohol.

Liquid organic amides are all those organic amides that are liquid at a temperature of 20° C. Preferred organic amides are dimethylformamide (DMF), methylethyl-formamide, N-methylpyrrolidone (N-MP), N,N-dimethylacetamide, tetramethyl-urea (TMU), 1,3-dimethyl-3,4,5,6-tetrahydro-2(1H)-pyrimidone (DMPU) and hexamethylphosphoric acid triamide (HMPT).

The group of chemicals that can be used according to the invention for a vitamin D release reagent have the common feature that they are amphiphilic compounds. The reagent composition for releasing vitamin D more preferably contains 7 to 20% of the said amphiphilic reagents.

The release reagent preferably contains DMSO, DMF, N-MP and/or DMPU.

In principle, mixtures of several of the amphiphilic reagents specified above, e.g., consisting of several liquid amides, can be present in a reagent composition according to the invention. Preferably only three, and more preferably only two, and also preferably only one of the amphiphilic reagents mentioned above are used.

It is also preferred that the pH of the reagent composition according to the invention is between pH 3.8 and pH 4.6, more preferably between pH 3.9 and pH 4.5 and also preferably between pH 4.0 and pH 4.5.

As mentioned above, the release reagent can additionally contain 0.7 to 7 volume percent of a short-chain (C1 to C3) alcohol. It has proven to be expedient when such a short-chain alcohol is also present in the release reagent. The proportion of short-chain alcohol is preferably 0.8 to 5 volume percent.

Short-chain alcohols within the sense of the present invention are methanol, ethanol, propanol and isopropanol. Ethanol has especially proven to be suitable as the short-chain alcohol, and it is therefore more preferred.

A preferred reagent composition for releasing vitamin D compounds from vitamin D-binding protein has a pH value of 3.8 to 4.8, contains 5 to 30 volume percent of one or more reagents selected from the group comprising dimethyl sulfoxide (DMSO) and a liquid organic amide as well as 0.7 to 8 volume percent of a short-chain (C1 to C3) alcohol.

With the exception of vitamin D itself, other known compounds from vitamin D metabolism bind to the vitamin D-binding protein. The gene coding for the vitamin D-binding protein occurs in the human population in the form of different alleles. It is known that the polypeptides coded by these alleles differ biochemically, i.e., they lead to different phenotypes. These biochemical differences also influence the binding and release of vitamin D compounds. The reagent composition according to the invention is suitable for releasing vitamin D compounds independently of the phenotype of the vitamin D-binding protein. Thus a preferred embodiment of the present invention is the use of a reagent composition according to the invention to release vitamin D compounds from vitamin D-binding protein or, as explained above, to release vitamin D compounds from complexes of vitamin D-binding protein and vitamin D compound.

The reagent composition according to the invention is additionally preferably used to release vitamin D compounds in those samples which contain or could contain different phenotypes of vitamin D-binding protein.

For the purpose of releasing vitamin D compounds from vitamin D-binding protein, the reagent composition according to the invention is mixed with the sample (preferably serum or plasma). The mixing ratio of release reagent to sample is preferably between 10:1 and 1:10.

Additionally it is preferred to mix about ⅓ to 3 parts by volume, more preferably ½ to 2 parts by volume release reagent with one part by volume sample.

The buffer composition and concentration are selected by a person skilled in the art such that the specified pH range and the desired concentrations of amphiphilic reagent are adjusted during the incubation with the immunological substance for vitamin D. The reagent composition according to the invention preferably contains 20 mM-400 mM buffer portion. This buffer portion is particularly preferably between 30 mM and 350 mM or between 50 mM and 300 mM.

In addition, the invention concerns a method for the immunological detection of a 25-hydroxyvitamin D compound comprising the steps: a) mixing the sample to be examined with a reagent for releasing vitamin D compounds from vitamin D-binding protein which results in a mixture that has a pH value of 3.8 to 4.8 and contains 5 to 20 volume percent of one or more amphiphilic reagent selected from the group comprising dimethyl sulfoxide (DMSO) and a liquid organic amide as well as optionally 0.5 to 5 volume percent of a short-chain (C1 to C3) alcohol and b) the immunological analysis of the mixture from a).

It is essential for the immunological detection of a 25-hydroxyvitamin D compound according to the present invention that the 25-hydroxyvitamin D compound (=analyte) from the sample is incubated with the immunological substance under the conditions stated above for the mixture. The pH is particularly preferably between pH 4.0 and pH 4.5 during this incubation. The concentration of the amphiphilic reagent selected according to the invention is preferably between 7 and 15 volume percent and more preferably between 8 and 12 volume percent during the incubation of the analyte with the immunological reagent. The short-chain alcohol is preferably present at a concentration of 0.7 to 1.5 volume percent and more preferably of 0.8 to 1.2 volume percent during the said incubation with the immunological reagent.

If not stated otherwise, the term "vitamin D compound" is to be understood to include all compounds which contain the backbone of vitamin $D_2$ or the backbone of vitamin $D_3$ according to the following structural Formulas I and II:

Formula I

Formula II

In the structural Formulas I and II, the positions of vitamin D are stated according to the steroid nomenclature. The 25-hydroxyvitamin D denotes vitamin D metabolites that are hydroxylated at position 25 of the structural Formulas I and II, i.e., the 25-hydroxyvitamin $D_2$ as well as the 25-hydroxyvitamin $D_3$. Additional 25-hydroxyvitamin D compounds are the 1,25- and 24,25-dihydroxyvitamin D forms.

1,25-Dihydroxyvitamin D refers to the active forms of vitamin D (the so-called D hormones) that have a hydroxylation at position 1 as well as at position 25 of the structural Formulas I and II.

Other known vitamin D metabolites are 24,25-dihydroxyvitamin $D_2$ and 24,25-dihydroxyvitamin $D_3$.

The immunological detection of a vitamin D compound is preferably carried out such that at least one 25-hydroxyvitamin D compound selected from the group comprising 25-hydroxyvitamin $D_2$, 25-hydroxyvitamin $D_3$, 1,25 dihydroxyvitamin $D_2$, and 1,25-dihydroxyvitamin $D_3$ is detected.

As already mentioned above, 25-hydroxyvitamin $D_2$ and 25-hydroxyvitamin $D_3$ are particularly relevant forms of vitamin D for diagnostics. In the method according to the invention, the detection of 25-hydroxyvitamin $D_2$ and/or 25-hydroxyvitamin $D_3$ is preferred.

In principle all proteinaceous binding partners such as antibodies or other specifically binding polypeptides that bind to one or more 25-hydroxyvitamin D compounds can be used as immunological materials. A prerequisite for use in the method described above for the detection of a 25-hydroxyvitamin D compound is only that binding to the 25-hydroxyvitamin D compound to be examined occurs under the selected incubation conditions.

The term antibody means polyclonal antibodies, monoclonal antibodies, antigen-binding fragments of these antibodies such as Fab fragments, F(ab)2' fragments, or single chain antibodies. Specific binding polypeptides are in particular binding partners such as those that can be obtained by means of phage display (McCafferty, J. et al., Nature 348 (1990) 552-554), recombinant DNA technologies (U.S. Pat. No. 4,816,567), or from recombinatorial antibody libraries (Larrick, J. W. and Fry, K. E. Hum. Antibod. Hybridomas, 2 (1991) 172-189). It is preferable to use polyclonal or monoclonal antibodies produced in the conventional manner or antigen-binding fragments thereof.

All known vitamin D metabolites are as such not immunogenic. The chemical activation of components from vitamin D metabolism as well as their coupling to carrier molecules or reporter groups is not trivial. Thus for a successful immunization it is essential to prepare a conjugate which, for example, contains a 25-hydroxyvitamin D as a hapten. The term hapten is understood by a person skilled in the art as a substance which per se is not immunogenic but by coupling to a larger carrier molecule is present in a form against which antibodies can be generated. Suitable carrier materials for the production of hapten conjugates are known to a person skilled in the art. Bovine serum albumin, β-galactosidase, or the so-called keyhole limpet hemocyanin (KLH) are usually used as carrier materials.

Various positions of the structures as they are shown in Formulas I and II are in principle suitable for activation and coupling to a carrier material. Coupling via position 3 of 25-hydroxyvitamin $D_2$ or 25-hydroxyvitamin $D_3$ has, for example, proven to be favorable for the generation of antibodies which bind a 25-hydroxyvitamin D in a suitable manner.

A process for producing antibodies which bind to 25-hydroxyvitamin $D_2$ as well as to 25-hydroxyvitamin $D_3$ is described in detail in the examples.

The reagent composition according to the invention has proven to be suitable for use in an automated test for 25-hydroxyvitamin D compounds. The present invention preferably concerns the use of a reagent composition according to the invention for releasing vitamin D compounds from vitamin D-binding protein especially in an immunological test for the determination of 25-hydroxyvitamin D compounds.

The test for 25-hydroxyvitamin D is preferably completely automated. Completely automated in this case means that the experimenter only has to place the sample on an automated analyzer and all further steps are automatically carried out by the analyzer. The completely automated test is particularly preferably carried out on an ELECSYS (Roche Diagnostics GmbH) analyzer.

The reagent composition according to the invention is preferably used in a method for the detection of 25-hydroxyvitamin $D_2$ and/or 25-hydroxyvitamin $D_3$.

The test is preferably carried out as a competitive immunoassay in which the reagent composition according to the invention is used as the so-called sample buffer, i.e., the sample is mixed with the reagent composition according to the invention. In such a competitive test, a vitamin D compound added in a defined amount to the test competes with the corresponding vitamin D compound from the sample for the binding sites of the detection antibody. The more vitamin D compound is present in the sample, the smaller is the detection signal.

The method for the immunological detection of a 25-hydroxyvitamin D compound can, based on the knowledge of the present invention, be carried out in various ways.

For example and in a preferred manner, the sample is firstly mixed with a reagent composition according to the invention and incubated before further test components are added.

In addition and in a preferred manner, the sample, the reagent composition according to the invention, and an immunological substance are mixed together directly, and subsequently an incubation is carried out.

It is also possible and preferred that the reagent composition according to the invention already contains the immunological substance. This means that in this embodiment, the reagent composition according to the invention additionally preferably contains a polyclonal or monoclonal antibody to 25-hydroxyvitamin D.

Many commercial test systems are based on the use of solid phases coated with avidin or streptavidin (SA), for example, SA-coated microtiter plates or SA-coated latices.

A biotinylated analyte derivative is, for example, bound to this SA solid phase before or during the test procedure. When detecting 25-hydroxyvitamin D this can, for example, be a biotinylated 25-hydroxyvitamin $D_2$ and/or a biotinylated 25-hydroxyvitamin $D_3$. When using an SA-coated solid phase, it is possible and preferred that the sample, the reagent composition according to the invention, a biotinylated 25-hydroxyvitamin D derivative, and an immunological substance are mixed and incubated together.

According to the teaching of the present invention, a person skilled in the art is able to put together a test kit which contains all components that are necessary to detect vitamin D compounds. In particular a preferred test kit for the detection of a vitamin D compound is characterized in that, in addition to an antibody against the vitamin D compound, such a kit comprises a reagent composition which has a pH value of 3.8 to 4.8 and contains 5 to 30 volume percent of one or more amphiphilic reagents selected from the group comprising dimethyl sulfoxide (DMSO) and a liquid organic amide as well as optionally 0.7 to 8 volume percent of a short chain (C1 to C3) alcohol.

The invention is further elucidated by the following examples and figures. The actual protective scope results from the claims attached to this invention.

Example 1

Synthesis of 25-hydroxyvitamin D3-3-hemisuccinate KLH

For this synthesis, 25-hydroxyvitamin $D_3$ was chemically activated at position 3 (cf. Formula II) and coupled to KLH as an immunogen support. This synthesis was carried out via the intermediate steps 25-hydroxyvitamin $D_3$-3-hemisuccinate and 25-hydroxyvitamin $D_3$-3-hemisuccinate-N-hydroxysuccinimide ester.

1.1 Preparation of 25-hydroxyvitamin $D_3$-3-hemisuccinate 10 mg (25 μmol) 25-hydroxyvitamin $D_2$ (Sigma-Aldrich, No. H-4014) was dissolved in 1 ml absolute pyridine and stirred for 4 days at room temperature in the dark with 125 mg (1.25 mmol) succinic anhydride. The reaction mixture was taken up in 10 ml ethyl acetate and in each case washed with 2×10 ml water, 0.1 M hydrochloric acid and subsequently again with water. The organic phase was dried using about 1 g anhydrous sodium sulfate, filtered, and the solvent was removed in a vacuum. The residual solid was dried in a high vacuum. 10.5 mg (yield: 84%) of a colourless solid was obtained.

1.2 Preparation of 25-hydroxyvitamin $D_3$-3-hemisuccinate-N-hydroxy-succinimide ester 10.0 mg (20 μmol) 25-hydroxyvitamin D3-3-hemisuccinate was dissolved in 7 ml anhydrous dichloromethane and admixed with 2.76 mg (24 μmol) N-hydroxysuccinimide and 3.72 mg (24 μmol) N(3-dimethylaminopropyl)-N'-ethyl-carbodiimide (EDC). It was stirred overnight under argon, the organic phase was then washed twice with 10 ml water, dried over about 1 g anhydrous sodium sulfate and filtered. The solvent was removed in a vacuum and the residual reaction product was dried for 3 h in a high vacuum. 11.3 mg (yield: 94%) N-hydroxysuccinimide ester was obtained which was used for the conjugation without further purification.

1.3 Synthesis of 25-hydroxyvitamin $D_3$-3-hemisuccinate-KLH 150 mg keyhole limpet hemocyanin (KLH; Sigma-Aldrich No. H 8283) was dissolved in 25 ml 0.1 M potassium phosphate buffer, pH 8.0, and 11.3 mg of the N-hydroxysuccinimide ester in 2 ml DMSO was added. It was stirred overnight at room temperature, the product was subsequently purified by means of a gel column (AcA 202, column volume 0.5 l; 0.1 M potassium phosphate buffer pH 7.0). The fractions containing the conjugated protein were detected by means of UV absorption ($\lambda$=256 nm) and pooled. 10% glycerol was added, and the grey opalescent solution was used for the immunization.

Example 2

Generation and Isolation of Antibodies Against 25-hydroxyvitamin $D_3$

2.1 Immunization

The antibodies were generated in sheep. The 25-hydroxyvitamin $D_3$-3-hemisuccinate KLH conjugate from Example 1 was used for the immunization. The immunization dosage was 0.1 mg per animal. The first immunization was carried out in complete Freund's adjuvant. Further immunizations took place at 4 week intervals in incomplete Freund's adjuvant for a period of 10 months. Serum was collected in the middle of each immunization interval.

2.2 Purification of the Polyclonal Sheep Antibodies

The lipid-containing components were removed from the serum of the sheep immunized with 25-hydroxyvitamin $D_3$-3-hemisuccinate-LKH conjugate with the aid of AEROSIL (Evonik Degussa GmbH) (1.5%). Subsequently the immunoglobulins were precipitated using ammonium sulfate (1.7 M). The precipitate was dialyzed against 15 mM potassium phosphate buffer containing 50 mM NaCl, pH 7.0 and subsequently purified chromatographically by DEAE SEPHAROSE (GE Healthcare Bio-Sciences AB). The IgG fraction (=PAB<25-hydroxyvitamin D3>S-IgG (DE) was obtained from the flow-through of this chromatography column.

2.3 Affinity Chromatography to Purify 25-hydroxyvitamin D-specific Antibodies An immunadsorber which contains conjugated 25-hydroxyvitamin $D_2$ as the specificity-determinant was prepared for the immunochromatographic purification of the polyclonal antibodies. The immunadsorber was obtained by the following steps:

a) Synthesis of hydroxyvitamin $D_2$-3-2'-cyanoethyl ether 20.6 mg (50 μmol) 25-hydroxyvitamin $D_2$ (Fluka No. 17937) was dissolved in a 25 ml three-necked round bottom flask with an internal thermometer in 10 ml dry acetonitrile under an argon atmosphere. 1.5 ml tert-butanol/acetonitrile (9:1) was added to the solution and cooled to 6° C. in an ice bath. Subsequently 820 μl of an acrylonitrile solution (86 μl acrylonitrile in 1.0 ml acetonitrile) was added and stirred for 15 minutes at 6° C. Then 205 μl of a potassium hydride solution (25 mg KH in 0.5 ml tert-butanol/acetonitrile 9:1) was added. A brief flocculation occurred after which a clear solution was obtained. The reaction solution was stirred for a further 45 minutes at 6° C. and subsequently for 60 minutes at 4° C.

Subsequently the reaction solution was diluted with 10 ml methyl-tert-butyl ether and washed twice with 10 ml $H_2O$ each time. The organic phase was dried with about 1 g anhydrous sodium sulfate, filtered over a G3 glass frit and evaporated on a rotary evaporator. It was dried in a high vacuum to form a viscous clear residue with a mass of about 55 mg.

b) Synthesis of hydroxyvitamin $D_2$-3-3-aminopropyl ether

The entire nitrile obtained above was dissolved in 15 ml diethyl ether and admixed with a suspension of 7.5 mg lithium hydride in 7.5 ml diethyl ether while stirring. The reaction mixture was stirred for 1 hour at room temperature. Afterwards a suspension of 38.4 lithium aluminium hydride in 6.6 ml diethyl ether was added. This resulted in a strong turbidity of the mixture. The reaction mixture was stirred for a further hour at room temperature, then the reaction mixture was cooled to 0-5° C. in an ice bath, and 35 ml water was carefully added. The pH was made strongly basic by addition of 6.6 ml 10 M potassium hydroxide solution.

It was extracted three times with 65 ml methyl-tert-butyl ether each time. The combined organic phases were dried using about 5 g anhydrous sodium sulfate, filtered, and evaporated at room temperature on a rotary evaporator. The residue was dried to mass constancy using an oil pump. The crude product was dissolved in 5 ml DMSO and 3.0 ml acetonitrile and purified by means of preparative HPLC.

eluant A=Millipore-H2O+0.1% trifluoroacetic acid;
eluant B=95% acetonitrile+5% Millipore-H2O+0.1% TFA;
gradient: from 50% B to 100% B in 100 min
flow rate: 30 ml/min
temperature: room temperature
column dimension: Ø=5.0 cm; L=25 cm;
column material: Vydac C18/300 Å/15-20 µm
det. wavelength: 226 nm Fractions whose product content was larger than 85% according to analytical HPLC (Vydac C18/300 Å/5 µm; 4.6×250 mm) were pooled in a round bottom flask and lyophilized. 13.7 mg (yield: 58%) was obtained as a colorless lyophilizate.

c) Synthesis of hydroxyvitamin $D_2$-3-3'-N-(hemisuberyl)aminopropyl-ether-N-hydroxysuccinimide ester 11.7 mg (25 µmol) of the amino derivative was dissolved in 5 ml freshly distilled DMF, and 92 mg (250 µmol) suberic acid-N-hydroxysuccinimide ester was added. 3.5 µl triethylamine was added, and the solution was stirred overnight under argon. The crude product was purified by preparative HPLC (conditions as above). 10.1 mg (yield: 56%) N-hydroxysuccinimide ester was obtained after lyophilization.

d) Synthesis of the hydroxyvitamin $D_2$ immunoadsorber 20 ml EAH SEPHAROSE (Amersham Biosciences, No. 17-0569-03) was washed with 200 ml 0.5 M sodium chloride solution on a G3 glass frit and equilibrated with 200 ml 0.03 M potassium phosphate buffer pH 7.1. After excess liquid has drained off through the frit, the suspension was taken up in 200 ml of the same buffer, and 1.7 mg (2.3 µmol) N-hydroxysuccinimide ester in 10 ml DMSO was added. The reaction mixture was agitated overnight at room temperature on a shaker. It was again transferred to a glass frit, allowed to drain, and washed with 500 ml 0.05 M potassium phosphate buffer/0.15 M sodium chloride, pH 7.0. After complete drainage, it was resuspended in 25 ml of the same buffer, and 0.15 ml of a 25% sodium azide solution was added for preservation.

e) Purification of the Antibodies 10 ml of the affinity matrix from d) was packed into a column and equilibrated with a buffer consisting of 50 mM potassium phosphate and 150 mM NaCl at a pH of 7.5 (PBS). 3.6 g of PAB<25-hydroxyvitamin $D_3$>S-IgG (DE) was loaded onto the column. The column was washed stepwise with PBS, 0.5 M NaCl solution containing 0.05% TWEEN 20 (ICI Americas Inc.) and 30 mM sodium chloride. The specifically bound immunoglobulin was detached from the affinity matrix with 3 mM HCl solution. The HCl eluate was dialyzed against 1 mM ethyl acetate and subsequently lyophilized. The lyophilisate was dissolved in PBS, aggregates were removed by chromatography on SUPERDEX 200 (GE Healthcare Bio-Sciences AB), and the immunoadsorbed polyclonal antibodies obtained in this manner were used in a further step. The immunoaffinity matrix was regenerated with 1 M propionic acid and preserved in a solution of PBS containing 0.9% sodium azide.

Example 3

Assays for the Detection of 25-hydroxyvitamin D

Commercial assays were used according to the manufacturers' instructions. The 25-hydroxyvitamin D determinations were carried out by means of HPLC (test for 25(OH) vitamin $D_3$, from the Immundiagnostik Company, Bensheim, order No. KC 3400) or by means of LC-MS-MS (Vogeser, M. et al., Clin. Chem. 50 (2004) 1415-1417) as described in the literature.

The preparation of the ingredients and the general test procedure for a new immunological test was described in the following:

3.1 Synthesis of hydroxyvitamin D2-3-3'-N-(hemisuberyl)aminopropyl-ether-biotin-(beta-Ala)-Glu-Glu-Lys(epsilon) conjugate (=Ag—Bi)

13.7 mg (25 µmol) hydroxyvitamin D2-3-3'-aminopropyl ether was dissolved in 3.5 ml DMSO, 28.7 mg (30 µmol) biotin-(beta-Ala)-Glu-Glu-Lys(epison)-hemi-suberate-N-hydroxysuccinimide ester (Roche Applied Science, No. 11866656) and 12.5 µl triethylamine were added, and it was stirred overnight at room temperature. The reaction solution was diluted with 4.5 ml DMSO, filtered through a 0.45 µm microfilter, and subsequently purified by means of preparative HPLC (conditions see example 2.3 b)). Fractions that contain more than 85% product according to analytical HPLC were pooled and lyophilized. 9.8 (yield: 30%) purified biotin conjugate was obtained.

3.2 Ruthenylation of Polyclonal Antibodies Against 25-hydroxyvitamin D (=PAB-Ru) Purified by Affinity Chromatography The affinity-purified antibodies according to example 2.3 e) were transferred to 100 mM potassium phosphate buffer, pH 8.5, and the protein concentration was adjusted to 1 mg/ml. The ruthenylation reagent (ruthenium (II) tris(bipyridyl)-N-hydroxysuccinimide ester) was dissolved in DMSO and added to the antibody solution at a molar ratio of 7.5 to 1. After a reaction time of 60 min, the reaction was stopped by addition of 1-lysine, and the excess labelling reagent was separated by gel permeation chromatography on SEPHADEX G25 (GE Healthcare Bio-Sciences AB).

3.3 Test Procedure in the Immunoassay

The sample was measured using the ELECSYS system from Roche Diagnostics GmbH. 25 µl sample was mixed with 30 µl release reagent (A) and simultaneously or sequentially with 15 µl ruthenylated detection antibody (B) and incubated for 9 minutes. In the next step, the biotinylated wall antigen (C) (50 µl) was added, and the pH value was kept in the desired range by further addition of release reagent (A) (50 µl). After a further 9 minutes incubation, the magnetizable polystyrene particles (D) coated with streptavidin (SA) (30 µl) were added, and after a further incubation for 9 minutes, the amount of bound ruthenylated antibody was determined as usual.

The release reagent (A) contained:
220 mM acetate buffer, pH 4.0
0.1% oxypyrion
0.1% MIT
1% EtOH
0.1% polydocanol
0.2% rabbit IgG
and an amphiphilic reagent when specified
Solution (B) with the ruthenylated <25-OH-vitamin D> antibody conjugate contained:
20 mM phosphate buffer, pH 6.5
0.1% oxypyrion
0.1% MIT (N-methylisothiazolone HCl)
1% EtOH (ethanol)
0.1% polydocanol
1% rabbit IgG (DET)
2.0 µg/ml PAB-Ru (from example 3.2)
as well as an amphiphilic reagent when specified
Solution (C) with the biotinylated wall antigen contained:
20 mM phosphate buffer, pH 6.5
0.1% oxypyrion
1% EtOH
0.1% polydocanol
0.2% rabbit IgG
0.18 µg/ml Ag—Bi (from example 3.1)
as well as an amphiphilic reagent when specified
The suspension with SA-coated latex particles (D) contained:
0.72 mg/ml SA-coated magnetizable polystyrene particles having a binding capacity of 470 ng/ml.

Example 4

Sample Incubation Buffer with/without Addition of an Amphiphilic Reagent

In prior experiments, it was observed that sera from humans of Caucasian descent and sera from humans of African descent behave differently in some test procedures for the detection of 25-hydroxyvitamin D. Normal sera from donors of different ethnic descent have therefore specifically been examined.

4.1 Comparison of Incubation Conditions with and without DMSO (Caucasians)

Figure 1:
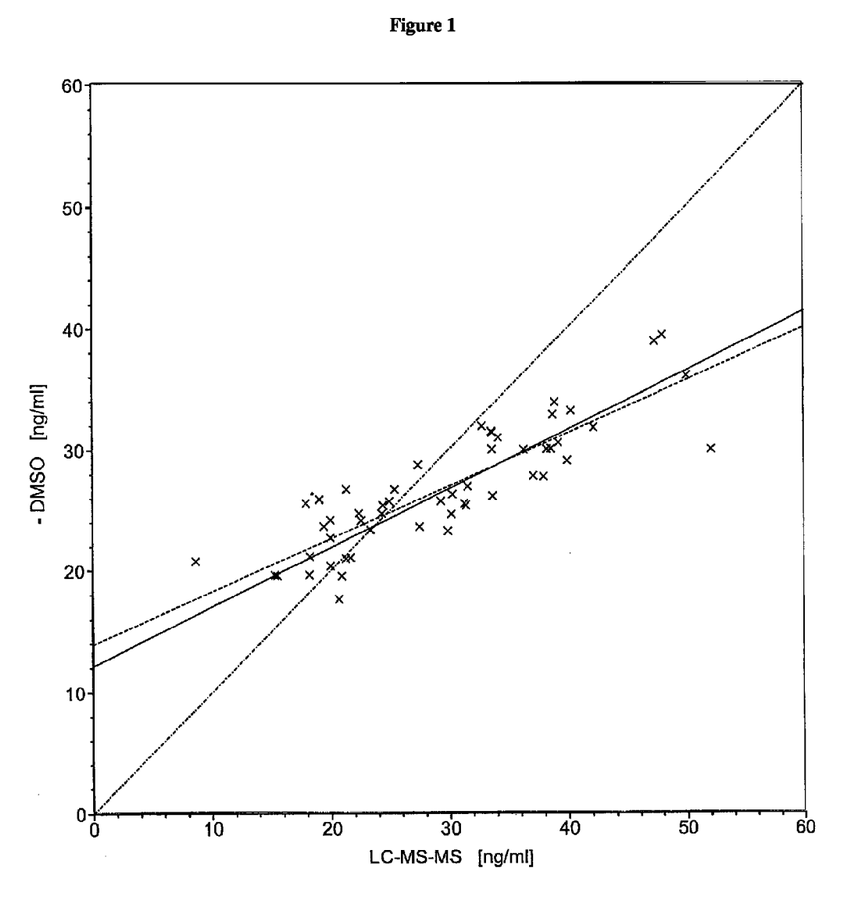
FIG. 1: Method comparison: Immunoassay (−DMSO) and LC-MS-MS. 25-Hydroxyvitamin D was determined by means of combined liquid chromatography and mass spectroscopy (LC-MS-MS) as well as by means of an immunoassay (IA) in which buffer without added DMSO (=−DMSO) was used for the incubation. The results in ng/ml for a total of 53 samples are plotted on the X axis for the LC-MS-MS and on the Y axis for the IA.
Figure 2:
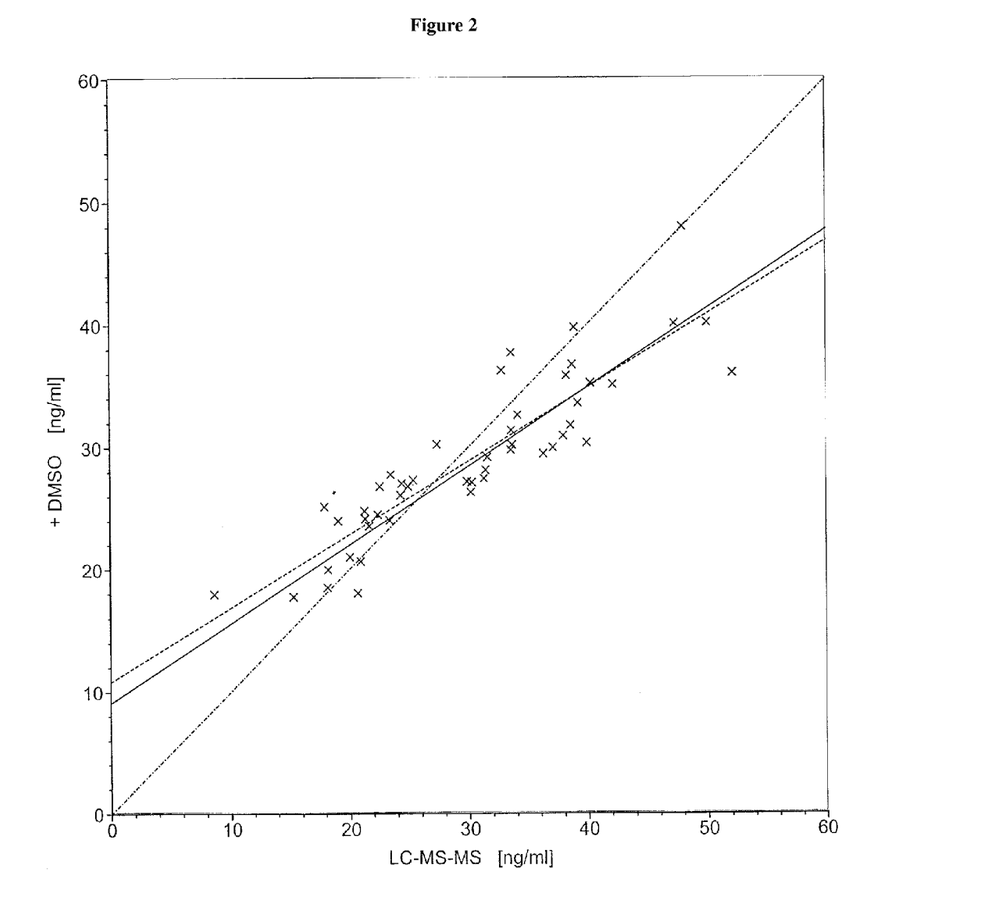
FIG. 2: Method comparison: Immunoassay (+DMSO) and LC-MS-MS. 25-Hydroxyvitamin D was determined by means of LC-MS-MS as well as by means of IA, where buffer containing DMSO (=+DMSO) was used for incubation in the IA. The results in ng/ml for a total of 48 samples are plotted on the X axis for the LC-MS-MS and on the Y axis for the IA.

The two following buffer compositions were used as the release reagent:
(a) release reagent (A), solution (B), and solution (C) (see example 3.3) without DMSO (=−DMSO) and
(b) release reagent (A), solution (B), and solution (C) which additionally contain 10% DMSO (=+DMSO).
A total of about 50 normal sera from humans of Caucasian descent were examined and compared to the standard method LC-MS-MS each time. As can be seen in FIG. 1, the values from the immunological test correlate with the LC-MS-MS (an r value of 0.86 was determined by means of linear regression). However, FIG. 1 also clearly shows that the slope of the regression line was very low (0.44 was calculated). This signifies a strongly falsified recovery of the samples.
A method comparison between LC-MS-MS and an immunological test using DMSO was shown in FIG. 2. A higher correlation (r=0.89) and a higher slope (0.60) were calculated in comparison to the reagent composition without DMSO.

4.2 Comparison of Incubation Conditions with/without DMSO (Caucasians Plus Africans)

Figure 3:
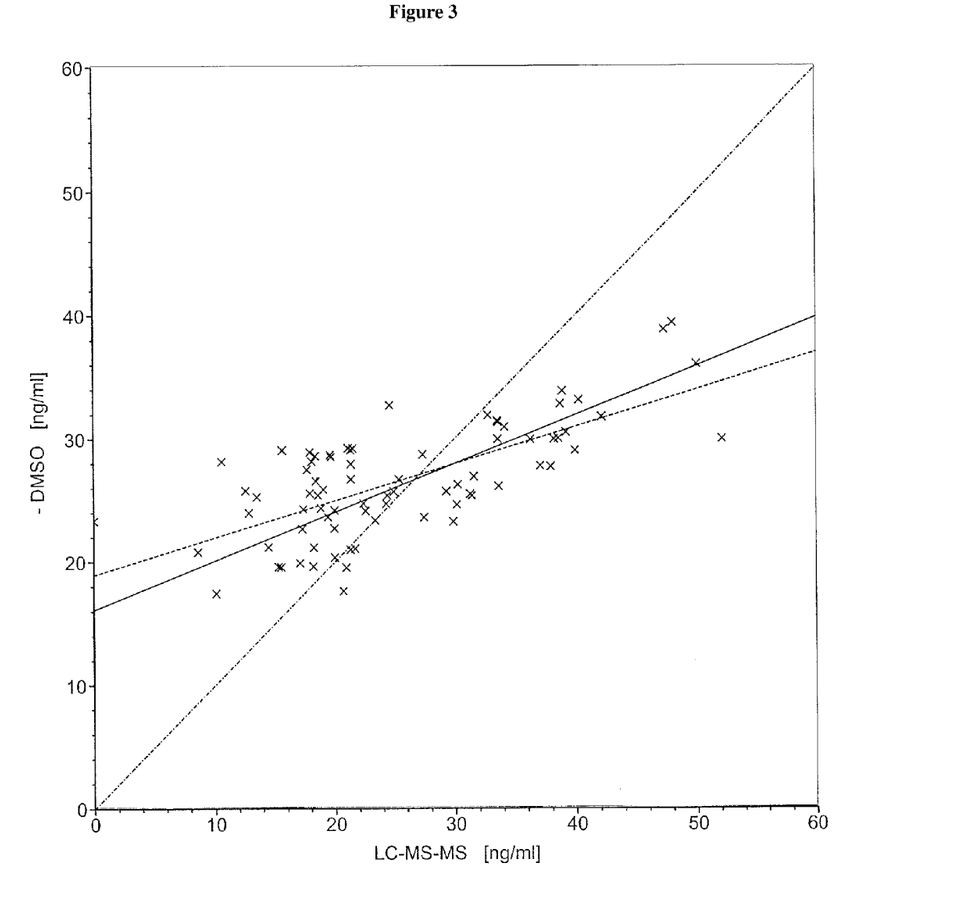
FIG. 3: Method comparison: Immunoassay (−DMSO) and LC-MS-MS. 25-Hydroxyvitamin D was determined by means of LC-MS-MS as well as by means of IA, where buffer without DMSO was used for the incubation in the IA. 31 Samples from persons of African descent were used as samples. The results in ng/ml for a total of 78 samples are plotted on the X axis for the LC-MS-MS and on the Y axis for the IA.
Figure 4:
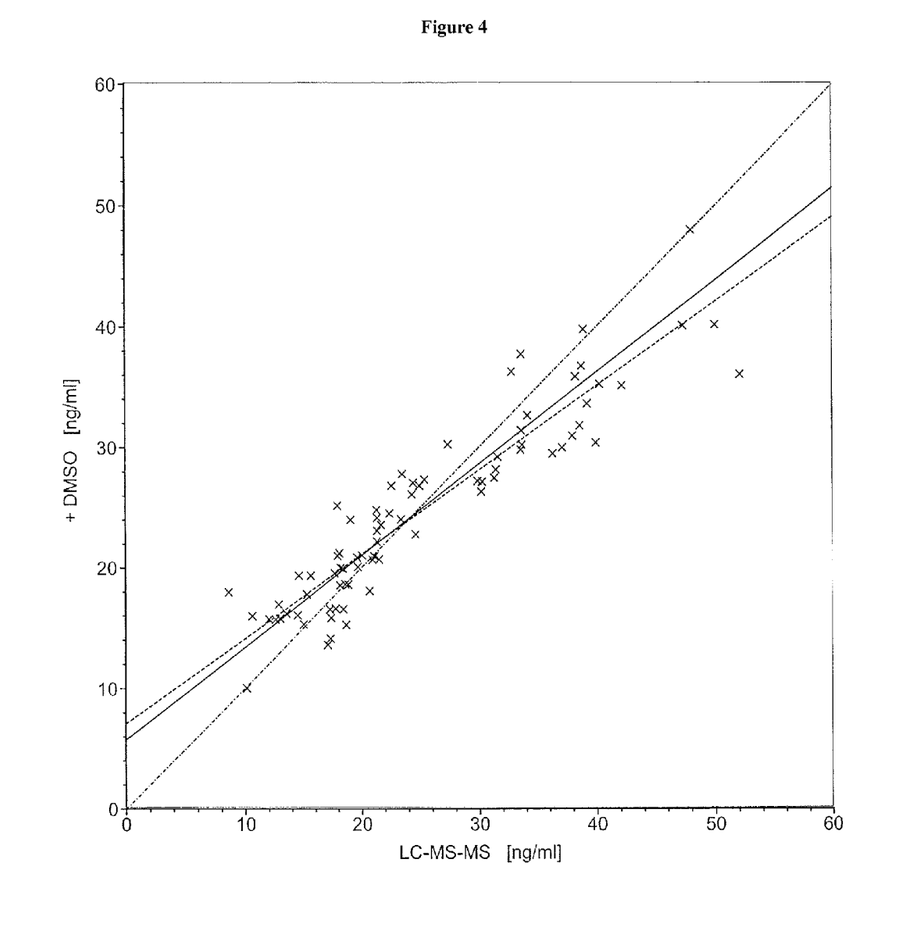
FIG. 4: Method comparison: Immunoassay (+DMSO) and LC-MS-MS. 25-Hydroxyvitamin D was determined by means of LC-MS-MS as well as by means of IA, where buffer containing DMSO was used for the incubation in the IA. Amongst others 31 samples from persons of African descent were used as the samples. The results in ng/ml for a total of 79 samples are plotted on the X axis for the LC-MS-MS and on the Y axis for the IA.

A total of 80 normal sera, of which about 50 were from people of Caucasian descent and 31 from people of African descent, were immunologically analyzed and compared with standard method LC-MS-MS each time. The same buffers (a) and (b) were used as in Example 4.1. As can be seen in FIG. 3, the values from the immunological test did not correlate very well with the LC-MS-MS. An r value of 0.69 was determined by means of linear regression. However, FIG. 3 also clearly shows that the slope of the regression line was very small (0.30 was calculated). This denotes a strongly falsified recovery of the samples.
A method comparison between LC-MS-MS and an immunological test using DMSO was shown in FIG. 4. A significantly higher correlation (r=0.93) as well as a greatly improved slope (0.70) were found compared to the reagent composition without DMSO.

Example 5

Comparison of Various Amphiphilic Reagents

Figure 5:
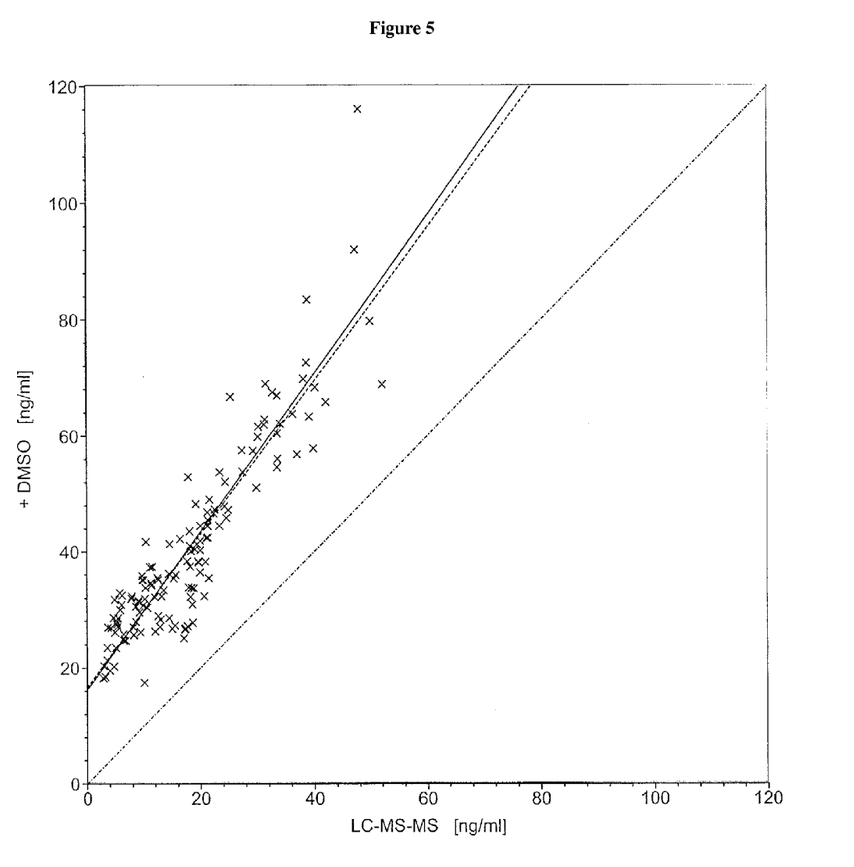
FIG. 5: Method comparison: Immunoassay (+DMSO) and LC-MS-MS. 25-Hydroxyvitamin D was determined by means of LC-MS-MS as well as by means of an IA, where buffer containing DMSO was used for the incubation in the IA. Amongst others 81 samples from persons of African descent were used as the samples. The results in ng/ml for a total of 136 samples are plotted on the X axis for the LC-MS-MS and on the Y axis for the IA.
Figure 6:
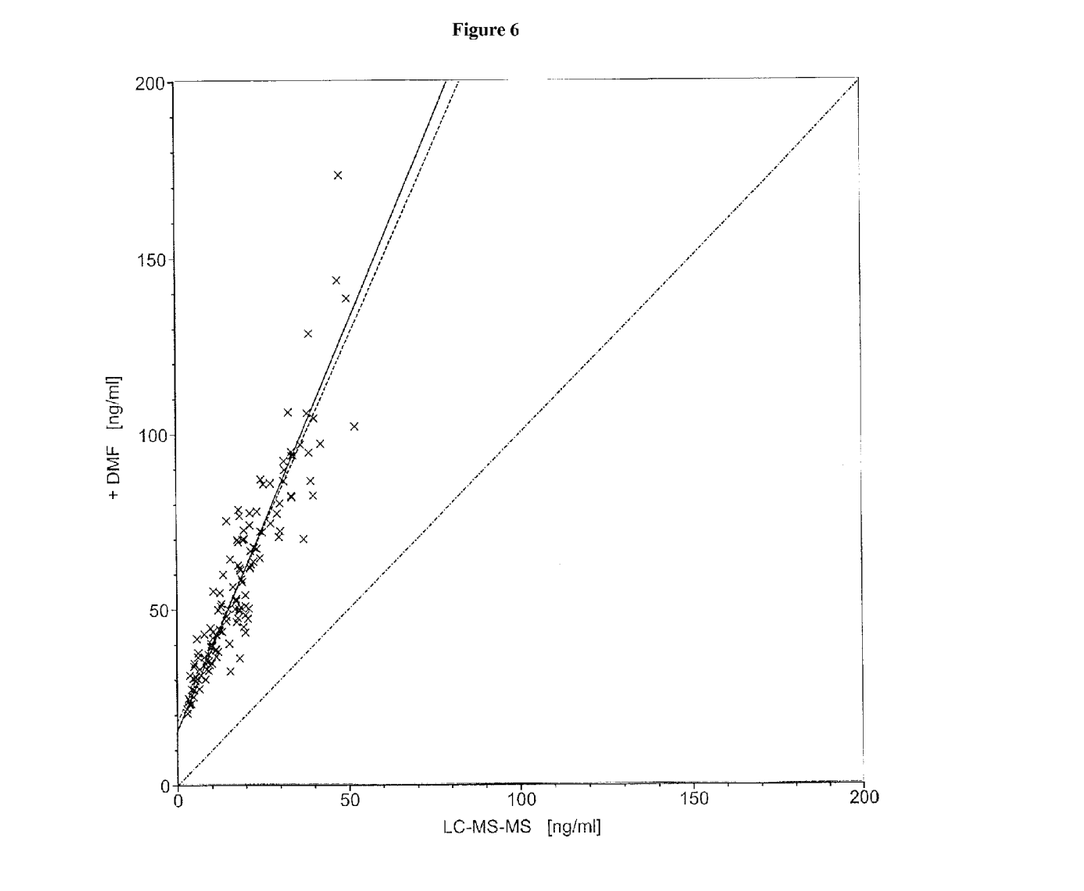
FIG. 6: Method comparison: Immunoassay (+DMF) and LC-MS-MS. 25-Hydroxyvitamin D was determined by means of LC-MS-MS as well as by means of an IA, where buffer containing dimethylformamide (=+DMF) was used for the incubation in the IA. Amongst others 81 samples from persons of African descent were used as the samples. The results in ng/ml for a total of 136 samples are plotted on the X axis for the LC-MS-MS and on the Y axis for the IA.
Figure 7:
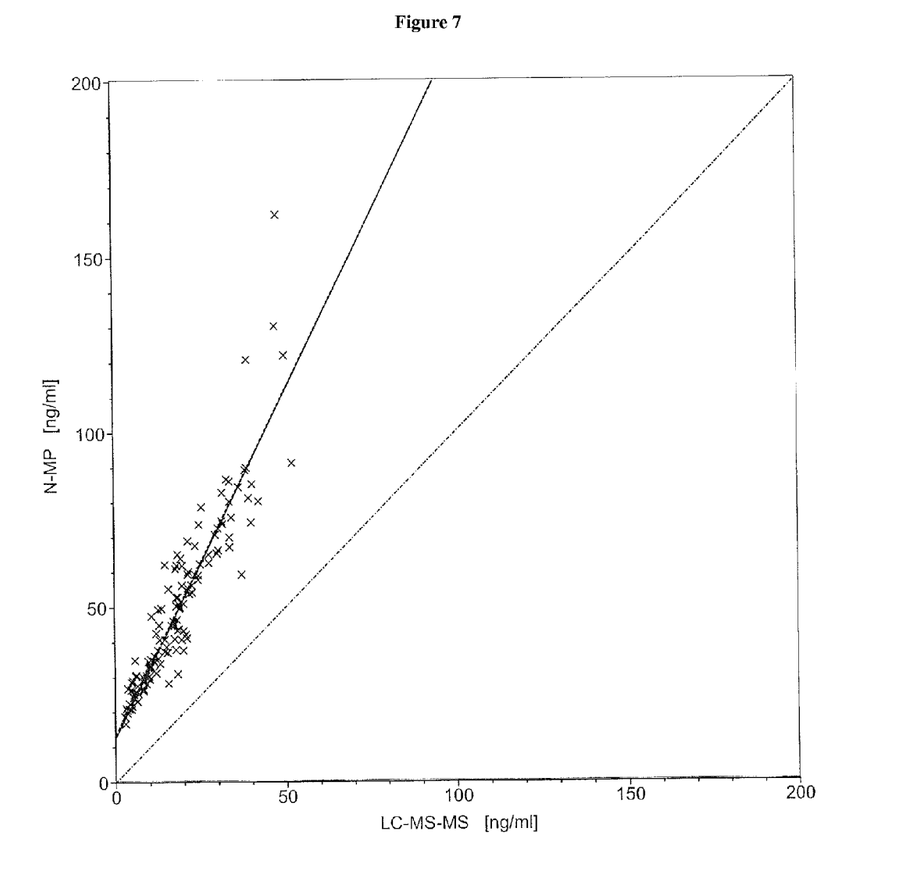
FIG. 7: Method comparison: Immunoassay (+N-MP) and LC-MS-MS. 25-Hydroxyvitamin D was determined by means of LC-MS-MS as well as by means of an IA, where buffer containing N-MP (=+N-MP) was used for the incubation in the IA. Amongst others 81 samples from persons of African descent were used as the samples. The results in ng/ml for a total of 135 samples are plotted on the X axis for the LC-MS-MS and on the Y axis for the IA.

The following buffer compositions were used:
(b) release reagent (A), solution (B), and solution (C) which additionally contain 10% DMSO (=+DMSO),
(c) release reagent (A), solution (B), and solution (C) which additionally contain 10% DMF (=+DMF), and
(d) release reagent (A), solution (B), and solution (C) which additionally contain 10% N-MP (=+N-MP).
About 135 normal sera from humans of various descent were examined using different reagent compositions to release vitamin D compounds from vitamin D-binding protein and compared to the standard method LC-MS-MS each time. As can be seen from FIGS. 5, 6, and 7, DMF and N-MP in addition to DMSO are also suitable as additives for a release reagent of vitamin D compounds. The values from the immunological test correlate very well with the LC-MS-MS for all three additives. r=values of 0.91 (buffer (b)), 0.92 (buffer (c)), and 0.92 (buffer (d)) respectively were determined using linear regression. Thus the reagent compositions according to the invention allow a determination of 25 hydroxyvitamin D that was independent of the phenotype of the vitamin D-binding protein.
Absolute values from the immunological test were determined in this example as well as in the previous example based on preliminary reference values and thus have no informative value. A reference standardization to determine reliable absolute values by means of LC-MS-MS still has to be carried out. The relative values show the significant test improvements achieved with reagent compositions according to the invention.

What is claimed is:
1. A method for releasing a vitamin D compound from a binding protein in a sample, the method comprising
combining the sample with a reagent composition having a pH of 3.8 to 4.8 and comprising one or more amphiphilic reagents selected from the group consisting of dimethyl sulfoxide (DMSO), dimethylformamide (DMF), N,N-dimethylacetamide, tetramethylurea (TMU), N-methylpyrrolidone (N-MP), 1,3-dimethyl-3,4,5,6-tetrahydro-2(1H)-pyrimidone (DMPU), and hexamethylphosphoric acid triamide (HMPT), wherein the one or more amphiphilic reagents are present in an amount of 5 to 30 volume percent, thereby releasing the vitamin D compound from the binding protein.
2. The method of claim 1 wherein the reagent composition further comprises 0.7 to 8 volume percent of an alcohol selected from the group consisting of methanol, ethanol, propanol, and isopropanol.

* * * * *